United States Patent [19]

Mathison

[11] Patent Number: 5,128,260
[45] Date of Patent: Jul. 7, 1992

[54] PROCESS FOR PREPARING CULTURE CONCENTRATES FOR DIRECT VAT SET DAIRY PRODUCTS PRODUCTION

[75] Inventor: Steven M. Mathison, Verona, Wis.

[73] Assignee: Sanofi Bio Ingredients, Inc., Waukesha, Wis.

[21] Appl. No.: 295,997

[22] Filed: Jan. 12, 1989

[51] Int. Cl.$^5$ .............................................. C12N 1/20
[52] U.S. Cl. ............................ 435/252.1; 435/252.4; 435/252.9; 435/253.6; 426/34; 426/40
[58] Field of Search ............ 435/252.4, 252.9, 253.4, 435/253.6, 261; 426/34, 40

[56] References Cited

U.S. PATENT DOCUMENTS 3,852,158  12/1974  Anderson et al. ................ 435/253.6
4,115,199  9/1978  Porubcan et al. ................ 435/252.9

*Primary Examiner*—Douglas W. Robinson
*Assistant Examiner*—Marian C. Knode
*Attorney, Agent, or Firm*—Bacon & Thomas

[57] ABSTRACT

The invention relates to a process of preparing concentrated bacterial cultures for direct vat inoculation of milk batches in which harmless lactic acid-producing bacteria are cultured in an aqueous medium including fermentation nutrients to obtain a fermented aqueous culture of the bacteria cells together with residual nutrients including casein, whereby the bacteria cells are recovered and concentrated by subjecting the bacterial culture to centrifugation while having dissolved therein prior to or after fermentation a combination of from 0.05% to 0.20% based on the weight of the culture of a water—soluble food—acceptable polyphosphate salt selected from the class consisting of tripolyphosphate and hexametaphosphate containing from 4 to 22 phosphate groups per molecule and from 0.25% to 0.50% based on the weight of the culture of a water—soluble food—acceptable citrate salt.

8 Claims, No Drawings

PROCESS FOR PREPARING CULTURE CONCENTRATES FOR DIRECT VAT SET DAIRY PRODUCTS PRODUCTION

This invention relates to culture concentrates for direct vat set dairy products production and is concerned with a process for producing the same.

Production of fermented dairy products such as cheese, yogurt, butter, milk and similar products require large numbers of active lactic acid-producing bacteria. Prior to the introduction of "direct inoculation to vat cultures", these large numbers of active bacteria were generated by growing the bacteria in question in a culture medium at the plant. This procedure was known as the bulk culture starter system. However, a fair amount of equipment, time and energy was required for production of bulk starter for plant use. Due to this, a direct inoculation to vat product was desirable from an "ease of use" standpoint.

Typical cell concentration of bulk starter is in range of $1 \times 10^9$ to $1 \times 10^{10}$ colony forming units (CFUs) per gram and the use rate is typically around 0.5-1% bulk starter on a w/w basis. In order for the direct inoculation to vat culture to work in the plant, much higher cell concentration are needed. This is because the inoculation rate for direct inoculation to vat is normally around 0.015 to 0.020% on a w/w basis. This is approximately 1.5% to 2% of bulk starter usage, so the typical cell concentration should be up to 100 times higher for direct inoculation to vat as compared to bulk starter.

When using a milk-based medium for growing the bacterial cells, there are residual solids, i.e. intact casein that are recovered in the "sludge" portion of centrifuged material along with the recovered cells. While this is not harmful to the cells, casein reduces the concentration potential of these cells. The prior art mentions the use of an enzyme treatment to improve concentration (U.S. Pat. No. 2,838,443).

In such a process protease enzymes are used to digest the casein resulting in smaller peptide units which are not recovered in the sludge. This is best done before inoculation and growth of the culture and could possibly decrease the proteolytic capacity of the grown culture.

The use of citrate ions to aid in cell recovery is also known. This is used to reduce the amount of casein recovered in the sludge along with the cells.

Similarly, U.S. Pat. No. 4,115,199 describes the use of a polyphosphate such as sodium hexametaphosphate (SHMP), to effectively recover high concentrations of bacterial cells without the casein. Using the process 98-100% of the cells can be recovered while achieving concentrations in the range of $50 \times 10^9$ to $200 \times 10^9$ CFUs per gram.

This patent also mentions the simultaneous use of 1% by weight sodium citrate and 4% by weight SHMP without obtaining any supplemental improvement since only $50 \times 10^9$ to $60 \times 10^9$ CFUs per gram were recovered.

In the course of the elaboration of the present invention preliminary trials were carried out in which 4% sodium citrate had been added to the growth medium after fermentation to solubilize the proteins and aid in centrifugation.

It was observed, from the results obtained, that the best concentration results of cells in the sludge portion of the centrifuged material were obtained when the fermented media contained low insoluble solids. This meant that the casein had been solubilized by the citrate and would centrifuge out in the effluent.

When the casein had not been totally solubilized, it was concentrated in the sludge portion along with the cells and so diluted the cell concentration causing problems.

It has now been quite unexpectedly found that a combination of a polyphosphate salt and a citrate salt, when added to the milk-based growth medium and in weaker concentrations than that used in the prior art, is capable of solubilizing the casein and so effectively promoting the recovery and concentration of bacterial cells from fermentation media.

A synergistic effect appeared to exist between such salts resulting in a nearly complete solubilization of casein.

According to the invention, the process of preparing concentrated bacterial cultures for direct vat inoculation of milk batches in which harmless lactic acid-producing bacteria are cultured in an aqueous medium including fermentation nutrients to obtain a fermented aqueous culture of the bacteria cells together with residual nutrients including casein, consists in dissolving in the culture medium, prior to the recovery and concentration of said cells by centrifugation, a combination of from 0.05% to 0.20% based on the weight of the culture of a water—soluble food—acceptable polyphosphate salt selected from the class consisting of tri-polyphosphate salt and hexametaphosphate salt and of from 0.25% to 0.50% based on the weight of the culture of a water—soluble food—acceptable citrate salt.

It is important that the polyphosphate salt/citrate salt combination dissolves the maximal amount of solids in the medium before centrifugation. For this purpose the polyphosphate salt/citrate salt combination can be added prior to or after the fermentation. Preferably, the whole combination in question is added prior to the fermentation since it has been observed that the low levels in polyphosphate salt/citrate salt required do not interfere in the normal fermentation process and do not inhibit the growth of the bacteria. In addition, the polyphosphate salt, when in sufficient amount, could control bacteriophage during fermentation.

The polyphosphate salt/citrate salt combination used in the process of the invention, when added prior to fermentation, provides, in fact, over a 90%-reduction in solids using several concentrations of polyphosphate salt and citrate salt.

Under such conditions, the culture growth even appears to be slightly enhanced both in activity and cell counts. This could be an added benefit from the pre-growth casein solubilization.

A hexametaphosphate salt, i.e. commercial mixture of polyphosphate salts containing 4 to 22 phosphate groups per molecule, can be cited as the polyphosphate salt particularly useful in the process of the invention.

Particularly desirable hexametaphosphate salt is that containing from 6 to 21 phosphate groups per molecule. Such glass phosphates are for instance those sold under trademarks of "HEXAPHOS" and "SODOPHOS" sold by FMC Corporation, New York, N.Y. (U.S.A.).

Generally, the polyphosphate salt and the citrate salt used in the process of the invention are in the form of their sodium salt. Particularly useful concentrations of polyphosphate salt are from 0.10 to 0.15% preferably 0.10% based on the weight of the culture.

Similarly the citrate salt is advantageously used at a concentration of 0.50% based on the weight of the culture.

In addition, a polyphosphate salt/citrate salt combination of 0.10%/0.50% is particularly preferred.

Classical nutrient media for culturing bacteria can be used which can be for instance an aqueous medium containing milk proteins added either as non-fat dry milk solids, or sweet whey solids, or both, fermentable carbohydrates such as glucose or lactose, growth stimulants such as yeast extracts, inorganic salts, buffers, etc . . .

Usually the medium contains from 4 to 12% nutrients.

The lactic acid-producing bacteria used in the process of the invention are for instance those employed for preparing cheese, yogurt, buttermilk, etc . . . Among these lactic acid-producing bacteria, the following ones can be cited:

Streptococcus lactis subsp. lactis,
Streptococcus lactis subsp. cremoris,
Streptococcus lactis subsp. diacetylactis,
Streptococcus thermophilus,
Lactobacillus delbrueckii subsp. bulgaricus,
Lactobacillus acidophilus,
Lactobacillus helevticus,
Bifidobacterium bifidum,
Lactobacillus casei subsp. casei,
Lactobacillus delbrueckii subsp. lactis,
Lactobacillus plantarum,
Lactobacillus delbrueckii subsp. delbrueckii,
Lactobacillus fermentum,
Pediococcus acidilactici,
Leuconostoc mesenteroides subsp. cremoris
(Bergey's Manual of Systematic Bacteriology, vol 1 - 1984; vol 2 - 1986)

The centrifugation step is generally carried out using classical equipment such as those usually employed for concentrating bacterial cells.

Using the process of the invention a very high recovery of the cells can be obtained, i.e. from 98 to 100% of the cells. In addition, the cell concentration will be at least $5 \times 10^{10}$ to $3 \times 10^{11}$ CFUs per gram.

As already set out hereabove, it is required that the feed solids be as low as possible to obtain a concentrated culture with acceptable culture activity and high cell numbers.

In this connection, comparative trials have been undertaken using either a polyphosphate salt or, in accordance with the invention, a combination of polyphosphate salt:citrate salt.

For this purpose, and aqueous nutrient medium was used which contained 6% non-fat dehydrated milk (NFDM), 1% lactose, 1% yeast extract. To this medium SHMP alone or combined with sodium citrate was added and allowed to react for 60 Min at 70° F. to solubilize the casein.

The results expressed in percents of residual solids in the involved media before fermentation were then determined:

TABLE

| Medium N° | % SHMP | % solids of media | | |
|---|---|---|---|---|
| | | 0% citrate | 0.25% citrate | 0.50% citrate |
| 1 | 0.05 | 0.59 | 0.28 | 0.14 |
| 2 | 0.10 | 0.54 | 0.16 | 0.02 |
| 3 | 0.15 | 0.29 | 0.10 | 0.02 |

TABLE-continued

| Medium N° | % SHMP | % solids of media | | |
|---|---|---|---|---|
| | | 0% citrate | 0.25% citrate | 0.50% citrate |
| 4 | 0.20 | 0.24 | 0.06 | 0.03 |

It can be concluded from this table that the addition of sodium citrate to the SHMP results in a substantial reduction in the residual solids of the medium before fermentation.

An additional comparison test made using 0.25% SHMP, described in U.S. Pat. No. 4,115,199, showed 0.27% of solids in the medium. Similarly, when no sodium citrate and no SHMP was present in the medium before fermentation, 0.82% of solids was registered.

In addition, when 0.25% or 0.50% sodium citrate was present in the pre-fermented medium, 0.38% and 0.31% of solids were registered respectively.

Taken together, these results show that a synergistic effect appears between the compounds in question which results in a nearly complete solubilization of casein.

The non-limitative following Example illustrates the process of the invention:

EXAMPLE

Preparation of a concentrate of Streptococcus cremoris or Streptococcus lactis for direct vat set dairy products production I - Growth medium (based on the weight of the medium)

78 lbs non-fat dry milk (6%)
13 lbs lactose (1%)
13 lbs yeast extract (1%)
1.3 lbs sodium hexametaphosphate (0.1%)
6.5 lbs sodium citrate (0.5%)
1200 lbs water (144 gallons)

II - Procedure

In a 150 gallon-mixing tank 78 lbs non-fat dry milk, 1.3 lbs SHMP and 6.5 lbs sodium citrate were added, at approximately 70° F., to 300 lbs (36 gallons) water. The mixture was agitated for 60 min and then 13 lbs lactose, 13 lbs yeast extract and 900 lbs (108 gallons) water were added. The medium was heated at 190°-200° F. for 60 min, cooled to 75° F. and the pH was adjusted to pH 6.7. The medium was then inoculated with 1% by volume of an active strain or mixed strain subculture and grown under pH control of 6.00-6.15 pH. After NH4OH neutralizer uptake has ceased, and the cell growth has stopped i.e. after 14-16 hours, the medium was cooled to 54° F. and centrifuged using a ALFA-LAVAL ® GYROTESTER ® centrifuge. Prior to and after centrifugation a count of CFUs per gram was undertaken together with a determination of the activity.

The activity was determined as follows:

A medium formed of non-fat dry milk at 11.5% solids heat treated for 30 minutes was inoculated with either 1% of pre-centrifuged growth medium or 0.1% of sludge obtained after centrifugation. The final pH was then registered 3 hours after inoculation at 32° C.

Using the above process concentrated bacterial cultures were obtained having the following characteristics:

|  | Activity (pH) | CFUs per gram | CFUs in II / CFUs in I |
|---|---|---|---|
| a) Strain subculture: *Streptococcus lactis* strain $L_4$ | | | |
| I* | 5.42 | $2.7 \times 10^9$ | 44 |
| II** | 4.87 | $1.2 \times 10^{11}$ | |
| b) Strain subculture: *Streptococcus lactis* strain $L_5$ | | | |
| I | 5.50 | $3.3 \times 10^9$ | 24 |
| II | 4.84 | $8.0 \times 10^{10}$ | |
| I | 5.60 | $3.3 \times 10^9$ | 36 |
| II | 4.93 | $1.2 \times 10^{11}$ | |
| c) Strain subculture: *Streptococcus lactis* strain B | | | |
| I | 5.62 | $8.4 \times 10^9$ | 21 |
| II | 5.03 | $1.8 \times 10^{11}$ | |
| d) Mixed strain subculture: *Streptococcus cremoris* strain 116/E8 | | | |
| I | 5.30 | $3.5 \times 10^9$ | 46 |
| II | 4.70 | $1.6 \times 10^{11}$ | |

[I*: prior to centrifugation (growth medium)]
[II**: after centrifugation (sludge)]

I claim:

1. A process of preparing concentrated bacterial cultures for direct vat inoculation of milk batches in which lactic acid-producing bacteria for the production of fermented dairy products are cultured in an aqueous medium including fermentation nutrients to obtain a fermented aqueous culture of the bacteria cells together with residual nutrients including casein, whereby said cells are recovered and concentrated by subjecting said culture to centrifugation wherein the improvement comprises dissolving therein prior to said fermentation a combination of from 0.05% to 0.20% based on the weight of the culture medium of a water-soluble, food acceptable hexametaphosphate salt containing from 4 to 22 phosphate groups per molecule and from 0.25% to 0.50% based on the weight of the culture medium of a water-soluble, food-acceptable citrate salt and whereby the medium is optionally heated for a time sufficient to dissolve casein.

2. A process according to claim 1 wherein the amount of hexametaphosphate salt is from 0.10% to 0.15%.

3. A process according to claim 1 wherein the combination is 0.10% hexametaphosphate salt and 0.50% citrate salt.

4. A process according to claim 1, wherein the hexametaphosphate salt contains from 6 to 21 phosphate groups per molecule.

5. A process according to claim 1 wherein the hexametaphosphate salt is sodium hexametaphosphate.

6. A process according to claim 1 wherein the centrifugation produces a cell concentration of bacteria having at least from $5 \times 10^{10}$ to $3 \times 10^{11}$ colony forming units per gram.

7. A process according to claim 1 wherein the citrate salt is sodium citrate.

8. A process according to claim 5 wherein the citrate salt is sodium citrate.

* * * * *